United States Patent [19]

Scholz et al.

[11] Patent Number: 4,995,899
[45] Date of Patent: Feb. 26, 1991

[54] OPTICALLY ACTIVE DIAZABICYCLOALKANE DERIVATIVES AND THEIR USE FOR PROTECTING CROPS FROM THE PHYTOTOXIC EFFECT OF HERBICIDES

[75] Inventors: Herbert Scholz, Neustadt; Adolf Zeidler, Ludwigshafen; Bruno Wuerzer, Otterstadt; Norbert Meyer, Ladenburg, all of Fed. Rep. of Germany

[73] Assignee: BASF Aktiengesellschaft, Ludwigshafen, Fed. Rep. of Germany

[21] Appl. No.: 334,814

[22] Filed: Apr. 6, 1989

Related U.S. Application Data

[63] Continuation of Ser. No. 3,708, Jan. 15, 1987, abandoned.

[51] Int. Cl.⁵ .................. A01N 43/54; A01N 43/50; C07D 487/04; C07D 471/04
[52] U.S. Cl. ..................................... 71/92; 540/473; 540/500; 544/282; 546/121; 548/324
[58] Field of Search ............... 71/92; 540/473, 500; 544/282; 546/121; 548/324

[56] References Cited

U.S. PATENT DOCUMENTS 4,021,224  5/1977  Pallos et al. ............... 544/124
4,448,960  5/1984  Rohr et al. ................. 548/324
4,618,361 10/1986  Moser ......................... 71/92

FOREIGN PATENT DOCUMENTS 65724   12/1982  European Pat. Off. ........... 548/324
1802468  5/1970  Fed. Rep. of Germany.

Primary Examiner—Mukund J. Shah
Assistant Examiner—E. Bernhardt
Attorney, Agent, or Firm—Keil & Weinkauf

[57] ABSTRACT

Diazabicycloalkane derivatives of the formula

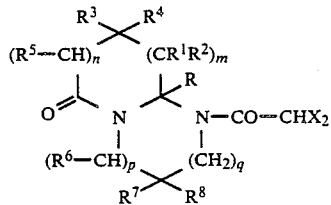

where R is alkyl, $R^1$, $R^2$, $R^3$, $R^4$, $R^5$, $R^6$, $R^7$ and $R^8$ are identical or different and independently of one another are each hydrogen or methyl, X is chlorine or bromine, m is 0 or 1, n is 1 or 2, and p and q are each 0, 1 or 2, the carbon atom functioning as bridgehead having an R configuration, and herbicidal agents containing acetanilides as herbididally active compounds and diazabicycloalkane derivatives as antagonistic agents.

3 Claims, No Drawings

OPTICALLY ACTIVE DIAZABICYCLOALKANE DERIVATIVES AND THEIR USE FOR PROTECTING CROPS FROM THE PHYTOTOXIC EFFECT OF HERBICIDES

This application is a continuation of application Ser. No. 003,708, filed on Jan. 15, 1987 now abandoned.

The present invention relates to optically active diazabicycloalkane derivatives, crop protection agents which contain these diazabicycloalkane derivatives, herbicides which contain acetanilides as herbicidal active ingredients and diazabicycloalkane derivatives as antagonistic agents, a method for protecting crops from the phytotoxic effect of herbicides based on acetanilides, and a method for selectively controlling undesirable plant growth using the stated herbicides.

Acetanilides of the formula III

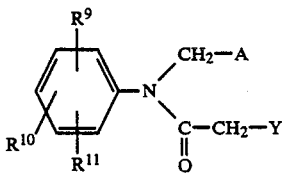

where $R^9$ is hydrogen, $C_1-C_5$-alkyl or $C_1-C_5$-alkoxy, $R^{10}$ and $R^{11}$ are identical or different and are each hydrogen, $C_1-C_5$-alkyl, $C_1-C_5$-alkoxy or halogen, Y is chlorine or bromine and A is $C_1-C_4$-alkoxy, $C_1-C_4$-alkoxyalkyl or an azole which is bonded via a ring nitrogen atom and is unsubstituted or substituted by halogen, phenyl, $C_1-C_4$-alkyl, $C_1-C_4$-alkoxy, $C_1-C_4$-alkylthio, $C_1-C_4$-perfluoroalkyl, cyano, carboxyl or $C_1-C_4$-alkoxy-carbonyl, and A may furthermore be a salt of an azole containing 2 or 3 nitrogen atoms, possess excellent herbicidal activity but damage the crop plants when used for example in corn, rice, sorghum or cereals (DE-A-2 648 008, DE-A-2 744 396, DE-A-2 305 495 and US-A-3 547 620).

EP-A-31 402 and EP-A-65 724 have disclosed herbicides which contain acetanilides of the formula III as the herbicidal active ingredient and racemic N-dihaloacetyldiazabicycloalkane derivatives as antagonists.

The N-dihaloacetyldiazabicycloalkane derivatives described there are racemates or diastereomer mixtures. Nothing is known to date concerning the biological action of the particular enantiomers or diastereomers.

We have found diazabicycloalkane derivatives of the formula I

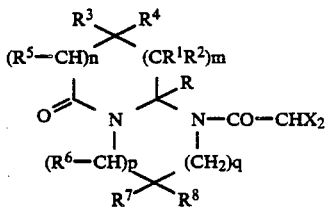

where R is $C_1-C_4$-alkyl, $R^1$, $R^2$, $R^3$, $R^4$, $R^5$, $R^6$, $R^7$ and $R^8$ are identical or different and independently of one another are each hydrogen or methyl, X is chlorine or bromine, m is 0 or 1, n is 1 or 2 and p and q are each 0, 1 or 2, the carbon atom functioning as the bridgehead and having an R configuration.

The novel diazabicycloalkane derivatives of the formula I can advantageously be used for increasing the toleration of crops for herbicidal acetanilides of the formula III.

Diazabicycloalkane derivatives of the formula I in which R is methyl or ethyl, in particular methyl, are preferred.

Examples of antagonistic optically active diazabicycloalkane derivatives of the formula I are 4-dichloroacetyl-5,7-dimethyl-8-oxo-1,4-diazabicyclo[3.3.0]octane, 5-dichloroacetyl-6,8-dimethyl-9-oxo-1,5-diazabicyclo[4.3.0]nonane, 5-dichloroacetyl-3,3,6,8-tetramethyl-9-oxo-1,5-diazabicyclo[4.3.0]nonane, 7-dichloroacetyl-3,6,8-trimethyl-2-oxo-1,7-diazabicyclo[4.3.0]nonane, 5-dichloroacetyl-6,9-dimethyl-10-oxo-1,5-diazabicyclo[4.4.0]decane, 5-dichloroacetyl-3,3,6,9-tetramethyl-10-oxo-1,5-diazabicyclo[4.4.0]decane, 4-dichloroacetyl-5-methyl-8-oxo-1,4-diazabicyclo[3.3.0]octane, 5-dichloroacetyl-6-methyl-9-oxo-1,5-diazabicyclo[4.3.0]nonane, 6-dichloroacetyl-7-methyl-10-oxo-1,6-diazabicyclo[5.3.0]decane, 5-dichloroacetyl-3,3,6-trimethyl-9-oxo-1,5-diazabicyclo[4.3.0]nonane, 5-dichloroacetyl-4,4,6-trimethyl-9-oxo-1,5-diazabicyclo[4.3.0]nonane, 5-dichloroacetyl-4,4,6-trimethyl-10-oxo-1,5-diazabicyclo[4.4.0]decane, 5-dichloroacetyl-3,3,6-trimethyl-10-oxo-1,5-diazabicyclo[4.4.0]decane and 4-dichloroacetyl-5,8-dimethyl-9-oxo-1,4-diazabicyclo[4.3.0]nonane.

Preferred compounds of the formula I are 5-dichloroacetyl-6-methyl-9-oxo-1,5-diazabicyclo[4.3.0]nonane and 4-dichloroacetyl-5-methyl-8-oxo-1,4-diazabicyclo[3.3.0]octane and 5-dichloroacetyl-3,3,6-trimethyl-9-oxo-1,5-diazabicyclo[4.3.0]nonane is particularly preferred.

In all of the compounds mentioned, the carbon atom functioning as the bridgehead has an R configuration.

The novel diazabicycloalkane derivatives of the formula I can be obtained by reacting an amine of the formula II

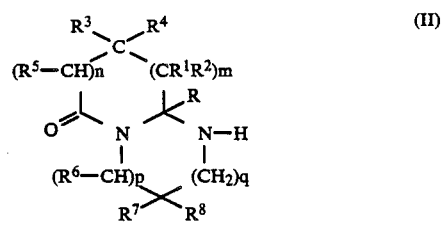

where R is $C_1-C_4$-alkyl, $R^1$, $R^2$, $R^3$, $R^4$, $R^5$, $R^6$, $R^7$ and $R^8$ are identical or different and independently of one another are each hydrogen or methyl, m is 0 or 1, n is 1 or 2 and p and q are each 0, 1 or 2, the carbon atom functioning as the bridgehead having an S configuration, with a dihaloacetyl chloride of the formula $X_2CH-COCl$, in which X is chlorine or bromine, in the presence of a hydrogen chloride-binding agent and of a solvent or diluent at from $-10°$ to $-50°$ C.

Suitable diluents or solvents are hydrocarbons and halohydrocarbons, such as toluene, xylenes, chlorobenzene, dichloromethane or ethylene chloride, ethers, such as diethyl ether, methyl tert-butyl ether, tetrahydrofuran or 1,4-dioxane, and nitriles, such as acetonitrile.

Suitable hydrogen halide-binding agents are alkali metal carbonates, alkali metal bicarbonates, aqueous solutions of alkali metal hydroxides, trialkylamines, N,N-dialkylanilines, such as N,N-dimethylaniline, and pyridine bases. The reaction is advantageously carried out using from 1 to 1.2 moles of dihaloacetyl chloride per mole of the amine of the formula II. From 1 to 1.2 moles of the hydrogen chloride-binding agent are added per mole of dihaloacetyl chloride.

Where X is chlorine, the novel diazabicycloalkane derivatives may furthermore be obtained by reacting an amine of the formula II with chloral hydrate in the presence of an acid acceptor and a catalytic amount of cyanide, which is added in the form of, for example, sodium cyanide or acetone cyanohydrin (DE-A-2 807 340).

Some of the racemates and diastereomer mixtures of amines of the formula II in which the carbon atom functioning as the bridgehead has either an R or an S configuration are disclosed in DE-A-1 802 468. They can be obtained by the preparation process described there, by reacting γ-oxo- or δ-oxocarboxylic acids or their esters with α,ω-alkylenediamines. For example, the racemate of 6-methyl-9-oxo-1,5-diazabicyclo[4.3.0]nonane can be prepared from ethyl lavulinate and propylenediamine.

The optically active amines of the formula II which are required for the novel process and in which the carbon atom functioning as the bridgehead has an S configuration in each case can be prepared by resolution of the above racemates or diastereomer mixtures by means of optically active acids.

Advantageously used optically active acids are chiral sulfonic acids, e.g. camphorsulfonic acid or bromocamphorsulfonic acid, and chiral hydroxycarboxylic acids and their derivatives, e.g. lactic acid, tartaric acid, diacetyltartaric acid, dibenzoyltartaric acid, malic acid or mandelic acid. Optically active hydroxycarboxylic acids are preferred, lactic acid and tartaric acid, especially D-(−)-lactic acid, being particularly noteworthy.

To prepare the diastereomeric salts from a racemic amine or a diastereomeric amine mixture and a chiral acid, these components are combined, in a suitable inert solvent, in a molar ratio of amine to acid of from 1:1 to 1:1.2, preferably 1:1, at from −20° to +50° C. After a stirring phase of up to 5 hours, during which the temperature is advantageously maintained at from −20° to +30° C., the diastereomeric amine salt which has crystallized out, and in which the carbon atom functioning as the bridgehead in the amine component has an S configuration, can be isolated.

Examples of suitable inert solvents for this step are alcohols, such as methanol, ethanol or isopropanol, and ethers, such as 1,2-dimethoxyethane, tert-butyl methyl ether, tetrahydrofuran or 1,4-dioxane, as well as aqueous mixtures of these solvents.

The diastereomeric amine salt which has been isolated and in which the amine component has the above configuration is washed with the solvent, and the desired amine is then liberated from the said salt. This is usually done in aqueous solution by adding a strong base, for example an aqueous solution of potassium hydroxide or sodium hydroxide. The desired amine is particularly advantageously liberated from the aqueous solution of the diastereomeric amine salt by means of a highly basic anion exchanger.

During this procedure, the amine of the formula II is usually present in aqueous solution and can be obtained in pure form by evaporating off the water under reduced pressure. The said amine can then be reacted directly with the appropriate dihaloacetyl chloride.

This process can be particularly advantageously used for the preparation and isolation of the diastereomeric lactate of the formula IV

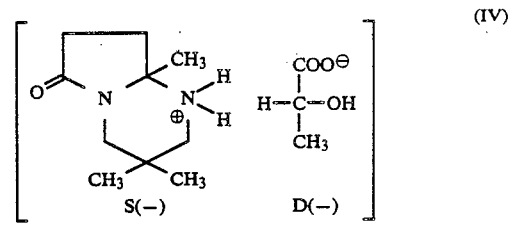

It is surprising that the amine components, which are aminals of geminal amines, do not undergo a cleavage reaction under the reaction conditions, i.e. when treated with an acid, since it is known that such aminals can usually be readily cleaved into a carbonyl compound and two amino components by acid catalysis (P.A.S. Smith, Open-Chain Nitrogen Compounds, vol. 1, page 322, W. A. Benjamin, Inc., New York, Amsterdam 1965). For example, Troeger's base undergoes racemization in an acidic medium (E. L. Eliel, Stereochemie der Kohlenstoffverbindungen, page 466, Verlag Chemie, Weinheim, 1965).

The amine salts which remain in the solution when the racemates or diastereomer mixtures are resolved, and in the amine component of which the carbon atom functioning as the bridgehead has the undesirable configuration, can be converted, by racemization, into mixtures in which the carbon atom functioning as the bridgehead has both an R and an S configuration. These mixtures can then be resolved again (recycling).

Surprisingly, the racemization reaction can also be carried out very advantageously using lactic acid (saving of steps). In this procedure, the amine salt in which the amine component has the wrong configuration is heated to 70°–105° C. in aqueous solution. After about 3–9 hours, racemization is complete, and the particular mixture can be obtained in pure form by evaporating the water.

This step can be carried out equally well with both the D(−)-lactate and the L(+)-lactate, the former being preferably used.

It is of course also possible to adopt the reverse procedure and use the amines of the formula II for resolving racemic lactic acid. We have found that both (L)-and (D)-3,6,6-trimethyl-9-oxo-1,5-diazabicyclo[4.3.0]nonane are particularly useful for this purpose.

The Examples which follow illustrate the invention.

EXAMPLE 1

3,3,6-Trimethyl-9-oxo-1,5-diazabicyclo[4.3.0]nonane D(−)-lactate (a) 20.5 g (0.113 mole) of racemic 3,3,6-trimethyl-9-oxo-1,5-diazabicyclo[4.3.0]nonane in 100 ml of tetrahydrofuran are initially taken. 14 g (0.113 mole) of purified, 75% strength by weight aqueous D(−)-lactic acid are added dropwise at room temperature, the mixture is stirred for 3 hours at room temperature and at 10° C., and the product is filtered off under suction and washed twice with cold tetrahydrofuran.

Yield: 28.6 g

Mp: 70°–72° C.
$(\alpha)_D^{20} = +3.5°$ (c=5; water)
(The concentration c is stated in each case in g per 100 ml of solvent.)

(b) 2740 g (1 mole) of purified 3.3% strength by weight aqueous D(−)-lactic acid are initially taken, and 182 g (1 mole) of racemic 3,3,6-trimethyl-9-oxo-1,5-diazabicyclo[4.3.0]nonane are introduced slowly at 22° C. The reaction is slightly exothermic, and the temperature increases to 25° C. Stirring is continued for 1 hour, and the mixture is evaporated down in a rotary evaporator at a maximum bath temperature of 70° C. and under 30 mm Hg. 277 g of residue are obtained in the form of a reddish oil, to which 300 ml of tetrahydrofuran are added while stirring. After about 1 hour, the suspension containing the precipitated colorless crystals is cooled to −5° C. and stirred for half an hour at this temperature, and the product is washed with 3×50 ml of tetrahydrofuran at −20° C. and dried in a drying oven at 50° C.
Yield: 252.2 g = 92.7%.

EXAMPLE 2

S(−)-3,3,6-Trimethyl-9-oxo-1,5-diazabicyclo[4.3.0]nonane D(−)-lactate 20 g of the lactate from Example 1 are dissolved in 500 ml of tetrahydrofuran, and the gently stirred solution is cooled to −20° C. After 3 hours, the precipitate is filtered off under suction.
Yield: 7.2 g
Mp.: 103°–105° C.
$(\alpha)_D^{20} = -10.70°$ (c=2; water)

EXAMPLE 3

S(+)-3,3,6-Trimethyl-9-oxo-1,5-diazabicyclo[4.3.0]nonane 4.7 g (0.017 mole) of the lactate from Example 2 are dissolved in 172 ml of water, and the solution is poured, in the course of 3 hours, over a column which has a diameter of 2 cm and a length of 36 cm and contains a strongly basic anion exchanger. After the solution has passed through, the column is washed at the same rate with 300 ml of water. The aqueous solutions collected are evaporated to dryness in a rotary evaporator, and the residue is dried overnight in a drying oven.
Yield: 3 g=95.5% of theory
Mp.: 88.5°–89° C.
$(\alpha)_D^{20} = +34.2°$ (c=2; water)

EXAMPLE 4

R(−)-5-Dichloroacetyl-3,3,6-trimethyl-9-oxo-1,5-diazabicyclo[4.3.0]nonane 3 g (0.01648 mole) of the amine from Example 3 and 1.9 g (0.0184 mole) of triethylamine in 16.5 ml of toluene are initially taken. 2.7 g (0.0179 mole) of dichloroacetyl chloride are added at from 30° to 35° C. in the course of 15 minutes, the mixture is stirred for 2 hours at 30° C., 16.5 ml of water are added and stirring is continued for 1 hour at 3° C. The product is filtered off under suction at room temperature and washed twice with 5 ml of water and twice with 4 ml of cold isopropanol.
Yield: 3.7 g = 77.1% of theory
Mp.: 170°–171° C.
$(\alpha)_D^{20} = -49°$ (c=2; CHCl$_3$)
Purity: 99% (HPLC)

EXAMPLE 5

3,3,6-Trimethyl-9-oxo-1,5-diazabicyclo[4.3.0]nonane L(+)-lactate

The procedure is similar to that described in Example 1, except that L(+)-lactic acid is used.
Mp. 71.5°–72° C.
$(\alpha)_D^{20} = -4.2°$ (c=5; water)

EXAMPLE 6

R(+)-3,3,6-Trimethyl-9-oxo-1,5-diazabicyclo[4.3.0]nonane L(+)-lactate

The procedure is similar to that described in Example 2, except that the L(+)-lactate from Example 2 is used.
Mp.: 103°–105.5° C.
$(\alpha)_D^{20} = +11.7°$ (c=2; water)

EXAMPLE 7

R(−)-3,3,6-Trimethyl-9-oxo-1,5-diazabicyclo[4.3.0]nonane

The procedure is similar to that described in Example 3, except that the L(+)-lactate from Example 6 is used.
Mp.: 88.5°–89.5° C.
$(\alpha)_D^{20} = -34.2°$ (c=2; water)

EXAMPLE 8

S(+)-5-Dichloroacetyl-3,3,6-trimethyl-9-oxo-1,5-diazabicyclo[4.3.0]nonane

The procedure is similar to that described in Example 4, except that the R(+)-amine from Example 7 is used.
Mp.: 168°–169.5° C.
$(\alpha)_D^{20} = +50.9°$ (c=2; CHCl$_3$)

EXAMPLE 9

Racemization of R-3,3,6-trimethyl-9-oxo-1,5-diazabicyclo[4.3.0]nonane D(−)-lactate 8 g of the stated lactate, $(\alpha)_D^{20} = +12°$ (c=2; water), in 400 ml of water are refluxed. The angle of rotation changes from +12° to +4.5° in the course of 6 hours. Evaporation to dryness gives a residue having a melting point of 68°–72° C.

EXAMPLE 10

4-Dichloroacetyl-5,8-dimethyl-9-oxo-1,4-diazabicyclo[4.3.0]nonane in which the bridgehead carbon atom has the R configuration (a) 124.2 g (0.75 mole) of methyl 2-methyl-5-oxohexanoate in 450 ml of n-heptane are initially taken. 52.2 g (0.87 mole) of ethylenediamine are then added dropwise at room temperature in the course of 10 minutes. As a result of the exothermic reaction, the temperature increases to 38° C. 49 ml of the lower phase (aqueous methanol) are separated off. The mixture is cooled to 2° C. and stirred for 1 hour, and the product is filtered off under suction, washed with cold n-heptane and dried. 116.3 g of racemic 5,8-dimethyl-9-oxo-1,4-diazabicyclo[4.3.0]nonane are obtained.
Mp.: 85°–87° C. (after recrystallization from cyclohexane).

(b) 52 g (0.31 mole) of racemic 5,8-dimethyl-9-oxo-1,4-diazabicyclo[4.3.0]nonane are dissolved in 200 ml of ethanol. A solution of 46.4 g (0.31 mole) of L(+)-tartaric acid in 520 ml of ethanol are added dropwise at room temperature, and the mixture is stirred for 1 hour and cooled to 5° C.

Yield: 89.1 g=90.4% of theory
Mp.: 152°–154.5° C.
$(\alpha)_D^{20} = +12.5°$ (c=1; water)

(c) The diastereomeric amine salt is obtained by fractional crystallization of 5,8-dimethyl-9-oxo-1,4-diazabicyclo[4.3.0]nonane L(+)-tartrate from isopropanol.

$(\alpha)_D^{20} = -7.7°$ (c=2; water)

(d) An aqueous solution of the tartrate from Example 10c is poured over an anion exchanger similarly to Example 3. Thereafter, 5.7 g (0.034 mole) of the resulting amine are initially taken in 50 ml of toluene together with 3.6 g (0.036 mole) of triethylamine. 5.1 g (0.034 mole) of dichloroacetyl chloride are added dropwise to the cold mixture at from 30° to 35° C., and stirring is continued for 1 hour. 50 ml of water are added, the mixture is stirred for half an hour and the phases are separated.

The toluene phase is washed with twice 50 ml of water and evaporated down in a rotary evaporator to give 6 g of a yellow oil, which is crystallized with a little tert-butyl methyl ether and washed with a small amount of the same ether.

Mp.: 113°–115° C.
$(\alpha)_D^{20} = -128°$ (c=1; acetone)

The racemate prepared in a similar manner has a melting point of 116°–117° C.

Acetanilides whose toleration by crops can be improved by the optically active diazabicycloalkane derivatives of the formula I are those of the formula III in which $R^9$ is hydrogen, $C_1$–$C_5$-alkyl, such as methyl, ethyl, n-propyl, isopropyl, n-butyl, sec-butyl, isobutyl, tert-butyl, n-pentyl or a branched pentyl radical, or $C_1$–$C_5$-alkoxy, such as methoxy, ethoxy, propoxy, butoxy or pentyloxy, $R^{10}$ and $R^{11}$ are each hydrogen, halogen, such as fluorine, chlorine, bromine or iodine, $C_1$–$C_5$-alkyl, such as methyl, ethyl, n-propyl, isopropyl, n-butyl, secbutyl, isobutyl, tert-butyl, n-pentyl or a branched pentyl radical, or $C_1$–$C_5$-alkoxy, such as methoxy, ethoxy, propoxy, butoxy or pentyloxy, Y is chlorine or bromine and A is $C_1$–$C_4$-alkoxy or $C_1$–$C_4$-alkoxyalkyl, such as methoxy, ethoxy, methoxymethyl or 2-methoxyethyl, or an azole which is bonded via a ring nitrogen atom, e.g. pyrrole, pyrazole, imidazole, 1,2,4-triazole, 1,2,3-triazole or tetrazole, which is unsubstituted or monosubstituted or polysubstited by halogen, phenyl, $C_1$–$C_4$-alkyl, $C_1$–$C_4$-alkoxy, $C_1$–$C_4$-alkylthio, $C_1$–$C_4$-perfluoroalkyl, cyano, carboxyl or $C_1$–$C_4$-alkoxycarbonyl.

Examples of substituted azoles A are 2,6-dimethylpyrrole, tetramethylpyrrole, 3(5)-methylpyrazole, 4-methylpyrazole, 3(5)-ethylpyrazole, 4-etnylpyrazole, 3(5)-isopropylpyrazole, 4-isopropylpyrazole, 3,5-dimethylpyrazole, 3,4,5-trimethylpyrazole, 3(5)-phenylpyrazole, 4-phenylpyrazole, 3,5-diphenylpyrazole, 3(5)-phenyl-5(3)-methylpyrazole, 3(5)-chloropyrazole, 4-chloropyrazole, 4-bromopyrazole, 3,5-dimethyl-4-chloropyrazole, 3,5-dimethyl-4-bromopyrazole, 4-chloro-3(5)-methylpyrazole, 4-methyl-3,5-dichloropyrazole, 3(5)-methyl-4,5(3)-dichloropyrazole, 3(5)-chloro-5(3)-methylpyrazole, 4-methoxypyrazole, 3(5)-methyl-5(3)-trifluoromethylpyrazole, 3(5)-methyl-5(3)-ethoxycarbonylpyrazole, 3(5)-methyl-5(3)-methylthio-4-methoxycarbonylpyrazole, 4-cyanopyrazole, 4,5-dichloroimidazole, 2-methyl-4,5-dichloroimidazole, 3(5)-methyl-1,2,4-triazole, 3,5-dimethyl-1,2,4-triazole, 3(5)-chloro-1,2,4-triazole, 3,5-dichloro-1,2,4-triazole, 4(5)-methyl-1,2,3-triazole, 5-methyltetrazole and 5-chlorotetrazole.

Where the azole contains 2 or 3 nitrogen atoms, the radical A may furthermore be bonded in the form of a salt to one of the conventional strong inorganic or organic acids, such as hydrochloric acid, nitric acid, sulfuric acid, trichloroacetic acid, methanesulfonic acid, perfluorohexanesulfonic acid or dodecylbenzenesulfonic acid.

Preferred acetanilides of the formula III are those in which $R^9$ is hydrogen, $R^{10}$ and $R^{11}$ independently of one another are each methyl or ethyl in the orthoposition, Y is chlorine and A is unsubstituted or methyl-substituted pyrazole or triazole, each of which is bonded via a ring nitrogen atom.

Examples of herbicidal chloroacetanilides are 2-chloro-2',6'-dimethyl-N-(pyrazol-1-ylmethyl)-acetanilide, 2-chloro-2',6'-dimethyl-N-(3,5-dimethylpyrazol-1-ylmethyl)acetanilide, 2-chloro-2',6'-diethyl-N-(pyrazol-1-ylmethyl)acetanilide, 2-chloro-6'-ethyl-N-(pyrazol-1-ylmethyl)acet-o-toluidide, 2-chloro-6'-ethyl-N-(3,5-dimethylpyrazol-1-ylmethyl)-acet-o-toluidide, 2-chloro-2',6'-dimethyl-N-(1,2,4-triazol-1-ylmethyl)-acetanilide, 2-chloro-6'-ethyl-N-(1,2,4-triazol-1-ylmethyl)-acet-o-toluidide, 2-chloro-2',6'-diethyl-N-(2"-propyloxyethyl)-acetanilide, 2-chloro-6'-ethyl-N-(2"-methoxy-1"-methylethyl)-acet-o-toluidide, 2-chloro-2',6'-diethyl-N-(butoxymethyl)-acetanilide, 2-chloro-6'-ethyl-N-(ethoxymethyl)-acet-o-toluidide, 2-chloro-2',6'-dimethyl-N-(2"-methoxyethyl)-acetanilide, 2-chloro-6'-ethyl-N-(2"-butoxy-1"-methylethyl)-acet-o-toluidide, 2-chloro-2',6'-diethyl-N-(methoxymethyl)acetanilide and 2-chloro-2',6'-diethyl-N-(ethoxycarbonylmethyl)-acetanilide.

Herbicidal active ingredients and compounds which act as antagonists (antidotes) and provide protection can be applied together or separately by conventional techniques for crop treatment agents. For example, they can be incorporated into the soil together or separately, before or after sowing. In the most common method of application they are applied to the soil surface directly after sowing or in the period between sowing and emergence of the young plants. Treatment during and after emergence of the crops is also possible. The antagonist can always be applied simultaneously with the herbicidal active ingredient. Separate application, where the antagonist is first applied to the field, followed by the herbicidal active ingredient, or vice versa, is also possible provided that the time between application of the two substances is not so long that the herbicidal active ingredient has already damaged the crops. The active ingredient and antagonist can be formulated, separately or together, as sprays in suspendable, emulsifiable or soluble form or as granules. It is also possible for the seeds of the crop plants to be treated with the antagonist prior to sowing. In this case, the herbicidal active ingredient is applied alone in a conventional manner.

For a specific acetanilide, different amounts of the antagonistic compound are required, depending on the crops to be treated in each case. The ratios in which the acetanilide and the diazabicycloalkane derivative can be employed may be varied within a fairly wide range. According to the invention, the weight ratio of the herbicidal acetanilide to the antagonistic diazabicycloalkane derivative is from 1:2 to 1:0.001, preferably from 1:0.25 to 1:0.005, in particular 1:0.01.

The agents according to the invention containing diazabicycloalkane derivatives may be applied for instance in the form of directly sprayable solutions, powders, suspensions (including high-percentage aqueous, oily or other suspensions), dispersions, emulsions, oil dispersions, pastes, dusts, broadcasting agents or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, and paraffin, tetrahydrocarbons such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols and octadecanols, salts of sulfated fatty alcohol glycol ethers, condensation products of sulfonated naphthalene and naphthalene derivatives with formaldehyde, condensation products of naphthalene or naphthalenesulfonic acids with phenol or formaldehyde, polyoxyethylene octylphenol ethers, ethoxylated isoctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate and ureas, and vegetable products such as grain flours, bark meal, wood meal and nutshell meal, cellulosic powders, etc.

The formulations contain from 0.1 to 95, and preferably from 0.5 to 90, % by weight of herbicidal active ingredient and antidote, or antidote on its own. The application rates for herbicidal active ingredient are from 0.1 to 0.5 kg/ha. This amount of active ingredient is applied either jointly or separately with such an amount of antidote that the weight ratio of active ingredient to antidote is, as stated above, from 1:2 to 1:0.001, preferably from 1:0.25 to 1:0.005, and especially from 1:0.25 to 1:0.01.

Examples of formulations are given below.

I. 40 parts by weight of a mixture consisting of 4 parts by weight of 2-chloro-2',6'-dimethyl-N-(pyrazol-1-yl-methyl)-acetanilide and 1 part by weight of R(—)-5-dichloroacetyl-3,6,6-trimethyl-9-oxo-1,5-diazabicyclo[4.3.0]nonane is intimately mixed with 10 parts by weight of the sodium salt of a phenolsulfonic acid-urea-formaldehyde condensate, 2 parts by weight of silica gel and 48 parts of water. A stable aqueous dispersion is obtained. Dilution with 100,000 parts by weight of water gives an aqueous dispersion containing 0.04 wt % of active ingredient.

II. 3 parts by weight of a mixture consisting of 1 part by weight of 2-chloro-2'-methyl-6'-ethyl-N-(pyrazol-1-yl-methyl)-acetanilide and 1 part by weight of R(—)-5-dichloroacetyl-3,6,6-trimethyl-9-oxo-1,5-diazabicyclo[4.3.0]nonane is intimately mixed with 97 parts by weight of particulate kaolin. A dust is obtained containing 3% by weight of active ingredient.

III. 30 parts by weight of a mixture consisting of 1 part by weight of 2-chloro-2'-methyl-6'-ethyl-N-(pyrazol-1-yl-methyl)-acetanilide and 2 parts by weight of R(—)-5-dichloroacetyl-3,6,6-trimethyl-9-oxo-1,5-diazabicyclo[4.3.0]nonane is intimately mixed with a mixture consisting of 92 parts by weight of powdered silica gel and 8 parts by weight of paraffin oil which has been sprayed onto the surface of this silica gel. A formulation of the active ingredient is obtained having good adherence.

IV. 20 parts by weight of a mixture consisting of 8 parts by weight of 2-chloro-2'-methyl-6'-ethyl-N-ethoxymethylacetanilide and 1 part by weight of R(—)-5-dichloroacetyl-3,6,6-trimethyl-9-oxo-1,5-diazabicyclo[4.3.0]nonane is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

V. 20 parts by weight of a mixture consisting of 10 parts by weight of 2-chloro-2',6'-dimethyl-N-(2-methoxymethyl)-acetanilide and 1 part by weight of R(—)-5-dichloroacetyl-3,6,6-trimethyl-9-oxo-1,5-diazabicyclo[4.3.0]nonane is dissolved in a mixture consisting of 40 parts by weight of cyclohexanone, 30 parts by weight of isobutanol, 20 parts by weight of the adduct of 7 moles of ethylene oxide and 1 mole of isoctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of active ingredient.

The novel herbicidal agents may also contain, in addition to acetanilide and diazabicycloalkane derivative, further herbicidal or growth-regulating active ingredients of different chemical structure, without the antagonistic effect being lost. They may for instance contain 2-chloro-4-ethylamino-6-isopropylamino-1,3,5-triazine, 2-(2-chloro-4-ethylamino-1,3,5-triazin-6-yl-amino)-2-methylpropionitrile and N-(1-ethyl-n-propyl)-2,6-dinitro-3,4-dimethylaniline.

The action of the herbicidal agents according to the invention and the antidotes contained therein is demonstrated by the following biological experiments. For comparison purposes, a herbicidal agent disclosed in EP-A-31,402 was used which contained, as herbicidal active ingredient, 2-chloro-2',6'-dimethyl-N-(pyrazol-1-yl-methyl)-acetanilide (A) and, as antagonistic agent, 5-dichloroacetyl-3,3,6-trimethyl-9-oxo-1,5-diazabicyclo[4.3.0]nonane in the form of a racemic mixture.

The experiments show that the tolerance of the herbicidal acetanilides by crop plants is decisively improved by combined application of the optically active diazabicycloalkane derivatives (dihaloacetamides) without any loss in herbicidal action.

In the greenhouse, plastic boxes (51×32×6 cm) were filled with a loamy sand (pH 7) containing 3.3% humus. Indian corn seeds were sown shallow in rows in this substrate, and *Echinochloa crus-galli* was broadcast as an unwanted grass.

Herbicide A was applied individually and in combination, and the antagonists were only applied in the stated mixtures. All applications were preemergence: the agents were emulsified or suspended in water as carrier, and sprayed through finely distributing nozzles immediately after sowing. The boxes were set up in the greenhouse in an average temperature range of 15° to 25° C.

These experiments were observed until the corn plants had developed 3 to 5 leaves. After this stage, no more damage by the herbicidal agents was to be expected.

The action of the agents was assessed on a 0 to 100 scale, 0 denoting normal emergence and development of the plants, with reference to the untreated control, and 100 denoting nonemergence or complete destruction.

The heavy damage to the crop plant Indian corn caused by herbicide A under the severe test conditions was considerably reduced by the antidote used for comparison purposes.

In the same mixture ratio with herbicide A, compound No. 4 eliminated the damage completely (see Table 1).

The novel optically active diazabicycloalkane derivatives have an action far superior to that of the racemic mixtures.

| Herbicidal active ingredient | Antagonist | Appl. rate | Test plants and % damage | |
|---|---|---|---|---|
| | | | Zea mays | Echin. crus-galli |
| A | — | 1.0 | 95 | 100 |
| | | 0.25 | 20 | 100 |
| A | 5-dichloroacetyl-3,3,6-trimethyl-9-oxo-1,5-diazabicyclo[4.3.0]-nonane (racemic mixture) | 1.0 + 0.25 | 15 | 100 |
| A | Example 4 | 1.0 + 0.25 | 0 | 100 |

We claim:

1. A method of protecting corn plants from the phytotoxic action of a herbicide selected from the group consisting of 2-chloro-2',6'-dimethyl-N-(pyrazol-1-yl-methyl)acetanilide and 2-chloro-2'-methyl-6'-ethyl-N-(ethoxymethyl)acetanilide, which method comprises treating corn plants, their seed or the location with an effective amount of optically active R(−)-5-dichloroacetyl-3,3,6-trimethyl-9-oxo-1,5-diazabicyclo[4.3.0]nonane.

2. The method of claim 1, wherein said herbicide is 2-chloro-2',6'-dimethyl-N-(pyrazol-1-yl-methyl)-acetanilide.

3. The method of claim 1, wherein said herbicide is 2-chloro-2'-methyl-6'-ethyl-N-(ethoxymethyl)-acetanilide.

* * * * *